United States Patent [19]

Dockner et al.

[11] Patent Number: 4,551,528

[45] Date of Patent: Nov. 5, 1985

[54] CARRYING OUT ORGANIC CONDENSATION REACTIONS AT ELEVATED TEMPERATURES BY FEEDING THE STARTING MATERIALS INTO THE BOTTOM OF A REACTOR CHARGED WITH MINERAL OIL FOLLOWED BY PRODUCT DISTILLATION

[75] Inventors: Toni Dockner, Meckenheim; Herbert Krug, Ludwigshafen, both of Fed. Rep. of Germany

[73] Assignee: BASF Aktiengesellschaft, Fed. Rep. of Germany

[21] Appl. No.: 558,442

[22] Filed: Dec. 6, 1983

[30] Foreign Application Priority Data

Dec. 7, 1982 [DE] Fed. Rep. of Germany ....... 3245109

[51] Int. Cl.$^4$ .............................................. C08G 12/06
[52] U.S. Cl. .................................. 544/242; 546/251; 548/347; 548/379
[58] Field of Search ...................... 544/242; 546/251; 548/347, 379

[56] References Cited

U.S. PATENT DOCUMENTS 4,231,757  11/1980  Davis ................................... 564/443
4,284,555   8/1981  Gold et al. .......................... 424/244
4,444,956   4/1984  Schaffhausen et al. ............. 525/164

*Primary Examiner*—Maurice J. Welsh
*Attorney, Agent, or Firm*—Keil & Weinkauf

[57] ABSTRACT

Organic condensation reactions are carried out at elevated temperatures by a method in which the starting material or materials are fed in, in gaseous form, at the bottom of a reactor charged with a mineral oil having a boiling point of not less than 150° C., or are fed in, in liquid form, at the bottom of the reactor, and the mineral oil is kept at a temperature which is no lower than the boiling points, of the starting materials introduced as liquids, which correspond to the partial pressures, of the said starting materials, resulting at the bottom of the reactor, and the product is taken off, in gaseous form, at the top of the reactor.

11 Claims, 1 Drawing Figure

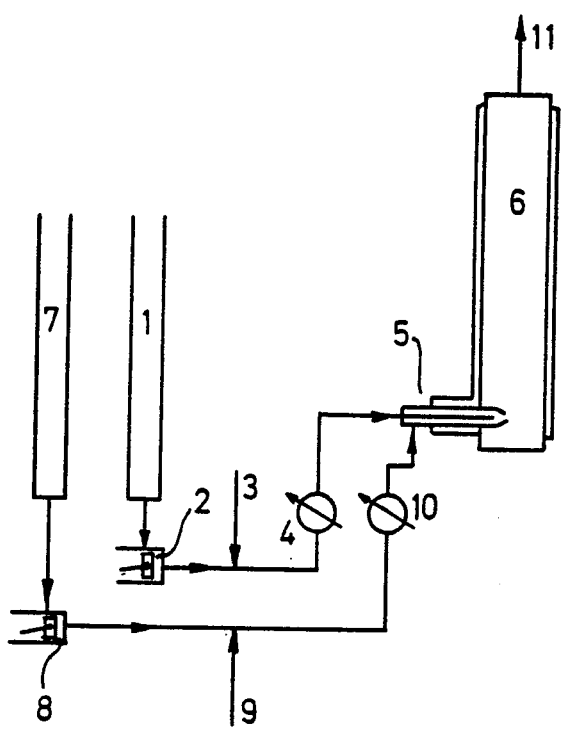

CARRYING OUT ORGANIC CONDENSATION REACTIONS AT ELEVATED TEMPERATURES BY FEEDING THE STARTING MATERIALS INTO THE BOTTOM OF A REACTOR CHARGED WITH MINERAL OIL FOLLOWED BY PRODUCT DISTILLATION

The present invention relates to a method of carrying out organic condensation reactions at elevated temperatures in a reactor charged with mineral oil.

It is known that organic condensation reactions can be carried out at elevated temperatures in the gas phase, the temperatures used being, as a rule, from 150° to 550° C. These relatively high temperatures readily lead to deposits of crack products in the reactors and other apparatuses, such as heat exchangers, and, where catalysts are used, on the catalyst surface. These deposits frequently result in interruptions in operation, when, for example, the reactor and the heat exchanger surfaces have to be cleaned, and the catalyst has to be changed or regenerated.

There was therefore a need for a method of carrying out organic condensation reactions, in which the disadvantages of the conventional methods can be avoided.

We have found an advantageous method of carrying out organic condensation reactions at elevated temperatures, wherein the starting material or materials are fed in, in gaseous form, at the bottom of a reactor charged with a mineral oil having a boiling point of not less than 150° C., or are fed in, in liquid form, at the bottom of the reactor, and the mineral oil is kept at a temperature which is no lower than the boiling points, of the starting materials introduced as liquids, which correspond to the partial pressures, of the said starting materials, resulting at the bottom of the reactor, and the product is separated by distillation. Preferably, the product is taken off, in gaseous form, at the top of the reactor and condensed.

The novel method makes it possible to carry out gas-phase reactions without decomposition products being deposited in the reactors. Particularly in the case of catalytic condensation reactions, the catalyst can be added in soluble or insoluble form to the mineral oil, so that, in contrast to conventional gas-phase reactions, coating of the surface of the catalyst and its deactivation, and the frequent interruptions in operation which are consequently required because the catalyst has to be changed or regenerated, can be avoided.

Examples of organic condensation reactions which can be carried out using the novel method are reactions in which monomeric compounds are formed from organic starting materials by eliminating $H_2O$ or $NH_3$ and forming carbon-nitrogen bonds and carbon-carbon bonds. In addition to the condensation reaction, other reactions, eg. addition reactions, may also participate in the formation of the products. In general, from 1 to 4 starting materials participate in the reaction. The products are preferably heterocyclic compounds, in particular 5-membered or 6-membered heterocyclic structures. Examples of useful organic condensation reactions are the conversion of hydrazine with acrolein to $\Delta^2$-pyrazoline,
N,N'-diformyl-1,2-diaminoethane to $\Delta^2$-imidazoline,
N,N'-diformyl-1,2-diaminopropane to 4-methyl-$\Delta^2$-imidazoline,
acrolein with ammonia to $\beta$-picoline,
N,N'-diformyl-1,3-diaminopropane to 1,2,3,4-tetrahydropyrimidine and
acetic acid with ethylenediamine to 2-methylimidazoline.

The method according to the invention is carried out as follows: the starting material or materials are fed in, in gaseous form, at the bottom of a reactor charged with a mineral oil having a boiling point of not less than 150° C., preferably not less than 200° C., in particular not less than 300° C., or are fed in, in liquid form, at the bottom of the reactor, and the mineral oil is kept at a temperature which is no lower than the boiling points, of the starting materials introduced as liquids, which correspond to the partial pressures, of the said starting materials, resulting at the bottom of the reactor, and the product is taken off, e.g. in gaseous form, at the top of the reactor. Examples of suitable mineral oils are high-boiling hydrocarbons or hydrocarbon fractions, such as gas oil, fuel oil, molten paraffin wax or an aromatic hydrocarbon oil. Vacuum gas oil which has a boiling point of not less than 350° C., and in particular boils within a range from 350° to 550° C., is preferably used.

Examples of suitable reactors for the condensation reaction are stirred kettles, but vertical cylindrical reactors, such as bubble tray columns, bubble columns or packed columns, are advantageously used for the novel method. Where several starting materials are involved in the reaction, it is also possible for one or more of the starting materials to be vaporized outside the reactor and introduced in gaseous form at the bottom of the reactor, and the remaining starting material or materials to be introduced in liquid form at the bottom of the reactor and vaporized there. It may be advantageous to dilute the vaporized starting material or materials with an inert gas. Examples of suitable inert gases are steam, carbon dioxide and, preferably, nitrogen.

The condensation reaction is carried out in general at from 100° to 500° C., preferably from 100° to 400° C., in particular from 150° to 350° C., under atmospheric or superatmospheric pressure, for example under a total pressure of not more than 10 bar. However, it is also possible to employ reduced pressure, for example a pressure as low as 100 mbar.

The condensation reaction can be carried out in the presence or absence of a condensation catalyst, depending on the type of reaction. Where a catalyst is used, this can be either soluble or insoluble in the mineral oil, insoluble catalysts advantageously being used in suspension in the mineral oil. However, catalysts in solution in the mineral oil are preferably used. Examples of useful condensation catalysts are acidic catalysts, eg. acidic ion exchangers, aromatic sulfonic acids, such as benzenesulfonic acid, toluenesulfonic acid or dodecylbenzenesulfonic acid, o-alkylphosphoric acids, phenols, such as alkylphenols, and picric acid, and basic catalysts, eg. primary, secondary and tertiary amine, such as tridecylamine, and basic ion exchangers. The catalysts which are soluble in the mineral oil are added to the latter in general in an amount of from 0.01 to 25, preferably from 0.1 to 10, in particular from 0.5 to 5, % by weight, based on the mineral oil.

The product are taken off in gaseous form at the top of the reactor and, advantageously, are then condensed. The condensation can be followed by a purification stage, for example distillation or fractionation. However, it is also possible to feed the gaseous products directly to a second reaction step.

The novel method can be carried out batchwise or continuously, a continuous procedure being preferred. In such a procedure, it may be advantageous for the mineral oil to be continuously fed in and withdrawn, for example where the reaction entails the formation of crack products. These crack products are discharged continuously from the reactor, together with the mineral oil. As a rule, it is not economical to work up and recycle the mineral oil removed since the latter is in general cheaply available, for example as fuel oil or vacuum gas oil. Advantageously, therefore, the mineral oil which is taken off and contains the crack products is burned, and fresh mineral oil is fed to the reactor.

The novel method is carried out by employing standard chemical processing equipment. For a typical arrangement of suitable apparatus, attention is directed to the accompanying drawing.

In accordance with this schematic representation, a first reactant in stock vessel 1, is fed to vaporizer 4 via metering pump 2 with nitrogen being added therebetween at line 3. From vaporizer 4, the gasified reactant is passed through nozzle 5 and into the bottom of reactor 6, which has been previously charged with mineral oil.

The same sequence is followed in regard to a second reactant which passes from container vessel 7 to vaporizer 10 via metering pump 8 with nitrogen being added from line 9. The vaporized second reactant is then likewise fed to nozzle 5 from where it enters the bottom of reactor 6. The gaseous product produced in the reactor is withdrawn at line 11 and passed to a condensor (not shown). The condensation may be followed by a distillation to purify the product.

The Examples which follow illustrate the invention.

EXAMPLE 1

155 g/hour of hydrazine hydrate are metered (cf. FIGURE) from a stock vessel 1 via a metering pump 2, 50 cm$^3$ (S.T.P.)/hour of nitrogen are added via line 3, and the mixture is fed into a vaporizer 4 heated at 120° C. From there it passes, in gaseous form, via a two-material nozzle 5 into a reactor 6 which is heated at 170° C. and charged with 1,300 g of vacuum gas oil having a boiling point of not less than 350° C. At the same time, 174 g hour of acrolein are metered from a stock vessel 7 via a metering pump 8, 50 cm$^3$ (S.T.P.)/hour of nitrogen are added via line 9, and the mixture is vaporized in a vaporizer 10° at 70° C., and passes from there, likewise in gaseous form, via a two-material nozzle 5 into the reactor 6. The reactor is a glass tube which is provided with a jacket and has a length of 1,300 mm and an internal diameter of 60 mm. The vacuum gas oil contains 1% by weight of dodecylbenzenesulfonic acid as a catalyst. The vapors leaving the reactor via line 11 are condensed, and collected in a glass flask. 321 g/hour of product containing 55.7% by weight of $\Delta^2$-pyrazoline are obtained, corresponding to a yield of 82.2%, based on hydrazine.

EXAMPLE 2

28 g/hour of N,N'-diformyl-1,2-diformyl-1,2-diaminoethane are metered from a stock vessel into a horizontal quartz vaporizer heated at 250° C., and the vapor is passed, together with 60 cm$^3$ (S.T.P.)/hour of nitrogen, into a reactor heated at 200° C. The reactor is an electrically heated quartz tube which is mounted vertically on the vaporizer, has a length of 500 mm and an internal diameter of 60 mm and is closed at the bottom with a fused-in quartz frit. The quartz tube is charged with 300 g of vacuum gas oil having a boiling point of not less than 350° C. The vapors leaving the reactor are condensed, and fractionally distilled. 30.7 g/hour (90% of theory) of $\Delta^2$-imidazoline of boiling point 105° C./32 mbar are obtained, the conversion being virtually quantitative.

EXAMPLE 3

300 g of vacuum gas oil having a boiling point of not less than 350° C. and, as the catalyst, 1% of tridecylamine are employed in the apparatus described in Example 2. 35 g/hour of N,N'-diformyl-1,2-diaminopropane together with 60 cm$^3$ (S.T.P.)/hour of nitrogen are heated at 250° C., and the resulting gaseous mixture is fed in at the bottom of the reactor, in which a reaction temperature of 190° C. is maintained. The gaseous product taken off at the top of the reactor is condensed and then fractionally distilled. 41.7 g/hour (92% of theory) of 4(5)-methyl-2-imidazoline of boiling point 94° C./20 mbar are obtained.

EXAMPLE 4

300 g of vacuum gas oil boiling within a range from 375° to 530° C. are employed in the apparatus described in Example 2. 20 g/hour of N,N'-diformyl-1,3-diaminopropane together with 70–80 l (S.T.P.)/hour of nitrogen are heated at 180° C., and the resulting gaseous mixture is fed, via a frit located at the bottom, into the reactor in which a reaction temperature of 200° C. is maintained. The gaseous product taken off at the top of the reactor and then condensed contains 9.5 g/hour (75% of theory) of 1,2,3,4-tetrahydropyrimidine.

EXAMPLE 5

56 g/hour of acrolein are metered from a stock vessel via a metering pump, 20 l (S.T.P.)/hour, measured using a rotometer, of nitrogen are added, and the mixture is fed in, via an immersion tube, at the bottom of a stirred flask which is heated at 250° C. and contains 1.3 kg of vacuum gas oil boiling within a range of from 375° to 530° C. and, as the catalyst, 5% by weight of dodecylbenzenesulfonic acid. At the same time, 10 l (S.T.P.) hour of ammonia are fed in, via a second immersion tube, likewise at the bottom of the stirred flask. The gaseous reaction mixture leaving the stirred flask is fed via a condenser kept at 150° C., in order to recycle entrained vacuum gas oil, and is then condensed. 49 g/hour (53% of theory) of $\beta$-picoline and 18 g/hour (22% of theory) of pyridine are obtained.

We claim:

1. A method of carrying out organic condensation reactions at elevated temperatures, wherein the starting material or materials are fed in, in gaseous form, at the bottom of a reactor charged with mineral oil having a boiling point of not less than 150° C., or are fed in, in liquid form, at the bottom of the reactor charged with mineral oil, and the mineral oil is kept at a temperature which is sufficiently high for the starting materials introduced as liquids at the bottom of the reactor to vaporize, and the product is obtained by distillation.

2. A method as claimed in claim 1, wherein the product is taken off in gaseous form at the top of the reactor.

3. A method as claimed in claim 1, wherein the starting materials are reacted in the mineral oil, fresh mineral oil is introduced where enrichment with by-products occurs, and the mineral oil enriched with by-products is removed.

4. A method as claimed in claim 3, wherein the mineral oil enriched with by-products is fed to a combustion stage.

5. A method as claimed in claim 1, wherein the mineral oil used is a high-boiling hydrocarbon fraction.

6. A method as claimed in claim 1, wherein the mineral oil used is a vacuum gas oil having a boiling point of not less than 350° C.

7. A method as claimed in claim 1, wherein the condensation reaction is carried out in a cylindrical reactor.

8. A method as claimed in claim 1, wherein a soluble or insoluble catalyst is added to the mineral oil.

9. A method as claimed in claim 1, wherein the procedure is carried out continuously.

10. A method as claimed in claim 1, wherein the mineral oil is continuously fed in and withdrawn.

11. A method as claimed in claim 1, wherein the reaction temperature maintained in the reactor is no lower than the boiling points, of the starting materials and products, which correspond to their partial pressures in the reactor.

* * * * *